United States Patent [19]

Fieselmann

[11] Patent Number: 4,777,023

[45] Date of Patent: Oct. 11, 1988

[54] PREPARATION OF SILICON AND GERMANIUM HYDRIDES CONTAINING TWO DIFFERENT GROUP 4A ATOMS

[75] Inventor: Benjamin F. Fieselmann, Bridgewater, N.J.

[73] Assignee: Solarex Corporation, Rockville, Md.

[21] Appl. No.: 830,103

[22] Filed: Feb. 18, 1986

[51] Int. Cl.⁴ ............................................. C01G 17/00
[52] U.S. Cl. ...................................... 423/89; 423/324; 423/414; 423/644
[58] Field of Search ................... 423/324, 414, 644, 89

[56] References Cited

U.S. PATENT DOCUMENTS

| | | | |
|---|---|---|---|
| 4,362,884 | 12/1982 | Arkles | 556/446 |
| 4,374,111 | 2/1983 | LeFrancois | 463/490 |
| 4,376,190 | 3/1983 | Schultz et al. | 525/333.1 |
| 4,379,766 | 4/1983 | Mack et al. | 260/413 |
| 4,423,238 | 12/1983 | Fenton | 549/368 |
| 4,480,009 | 10/1984 | Berger | 428/450 |
| 4,548,917 | 10/1985 | Lepage et al. | 502/150 |

FOREIGN PATENT DOCUMENTS

| | | | |
|---|---|---|---|
| 24926 | 3/1981 | European Pat. Off. | 7/8 |
| 18545 | of 1978 | Japan | 7/8 |
| 569534 | 4/1977 | U.S.S.R. | 423/324 |

OTHER PUBLICATIONS

Morrison et al., "Synthesis and Characterization of the (Halosilyl) Methyl-Silanes," Journal of Organometallic Chemistry (1975) vol. 92, pp. 163–168.
Ring et al., "Preparation and Reactions of Potassium Silyl," J. Am. Chem. Soc. (1960) vol. 83, pp. 802–805.
Varma et al., "A New Synthesis of Germylsilane," Angew. Chem. Internat. Edit. (1964) vol. 3, No. 8, p. 586.
Andrews et al., "Further Studies on the Silicon–Germanium Hydrides," J. Chem. Soc. (A) (1966) pp. 46–48.
Gokhale et al., "Synthesis of the Higher Silanes and Germanes," J. Inorg. Nucl. Chem. (1965) vol. 27, pp. 1911–1916.
Spanier et al., "Synthesis of Germylsilane from Silane and Germane in a Silent Electric Discharge," Inorg. Chem. (1963) vo. 2, pp. 215–216.
Timms et al., "The Silicon–Germanium Hydrides," J. Chem. Soc. (1964) pp. 1467–1475.
Phillips et al., "Some Applications of Gas Chromatography in Inorganic Chemistry," J. Anal. Chem. (Apr. 1963) vol. 35, No. 4, pp. 505–510.
Mackay et al., "Silicon–Germanium Hydrides," $Si_2GeH_8$," J. Chem. Soc. (A) vol. 19, pp. 2937–2942 (1969).
Benkeser et al., "Sylation of Organic Halides. A New Method of Forming the Carbon–Silicon Bond," J. Am. Chem. Soc. vol. 91, No. 13, pp. 3666–3667 (1969).
Choo et al., "Silicon- and Germanium-Substitution in Silylgermane, $H_3SiGeH_3$, " J. Chem. Research (S), 1981, 76, J. Chem. Research (M), 1981, 920–933.
Schenk et al., "Preparative Inorganic Chemistry, Brauer," pp. 664–665.
Bravo-Zhitvotovskii, et al., "Complexation of Triethylsilyllithium and its Analogs with Donor Ligands," Izv. Akad. Nauk. SSSR, Ser. Khim. No. 11, pp. 2560–2651 (1979).
Bullard et al., "Compounds of the Triphenyltin (II) Ion," Aust. Chem. (1981) vol. 34, pp. 1337–1340.
Power et al., "Mononuclear Lithium Amides using a Crown Ether: X-Ray Crystal Structure of Lithium Bis(Trimethylsilyl)Amide 12–Crown–4,[$LiN(SiMe_3)_2$ 12–Crown–4]," J. Chem. Soc., Chem. Commun., 1984 pp. 358–359.
Dye et al., "Solubilization of Alkali Metals in Tetrahydrofuran and Diethyl Ether by Use of a Cyclic Polyether," J. Am. Chem. Soc. vol. 92, No. 17, pp. 5226–5228 (1970).

Primary Examiner—John Doll
Assistant Examiner—Jackson Leeds
Attorney, Agent, or Firm—Finnegan, Henderson, Farabow, Garrett & Dunner

[57] ABSTRACT

A method for preparing a hydride containing at least two different Group 4A atoms wherein at least one of the Group 4A atoms is silicon or germanium. The method includes the steps of reacting an alkali metal and a macrocyclic compound with a silicon or germanium hydride to form a salt. The salt is then reacted with a Group 4A halide. The resulting hydrides are useful as deposition feedstock material for use in the formation of hydrogenated amorphous silicon alloy in the fabrication of photovoltaic devices and other semiconductor devices.

15 Claims, 1 Drawing Sheet

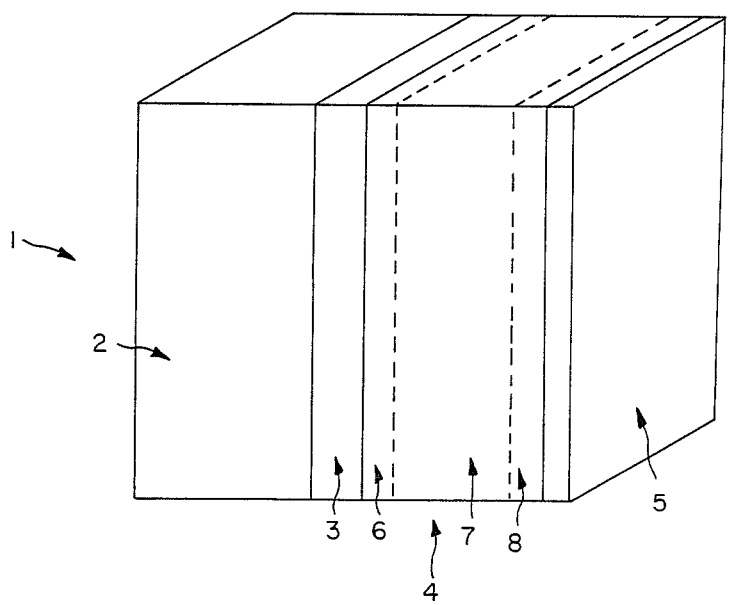

PREPARATION OF SILICON AND GERMANIUM HYDRIDES CONTAINING TWO DIFFERENT GROUP 4A ATOMS

BACKGROUND OF THE INVENTION

The present invention relates to a method for preparing hydrides containing at least two different atoms from Group 4A of the Periodic Table wherein at least one of the Group 4A atoms is silicon or germanium. Such hydrides can be used as deposition feedstock materials for the formation of hydrogenated amorphous silicon alloy films in the fabrication of photovoltaic devices and other semiconductor devices.

A number of different ways for making silicon and germanium hydrides containing two different Group 4A atoms have been reported in the literature. In one method, mixtures of different Group 4A hydrides are fed into a silent electronic discharge, sometimes referred to as an ozonizer-typ electric discharge. See T. D. Andrews and C. S. G. Phillips, "Further Studies on the Silicon-Germanium Hydrides," J. CHEM. SOC. (A) (1966) pp. 46–48; S. D. Gokhale, J. E. Drake and W. L. Jolly, "Synthesis of the Higher Silanes and Germanes," J. INORG. NUCL. CHEM. (1965) Vol. 27, pp. 1911–1916; E. J. Spanier and A. G. MacDiarmid, "The Synthesis of Germylsilane from Silane and Germane in a Silent Electric Discharge," INORG. CHEM. (1963) Vol. 2, pp. 215–216.

In another method, alloys of magnesium and different Group 4A metals are reacted with acid. See P. L. Timms, C. C. Simpson and C. S. G. Phillips, "The Silicon-Germanium Hydrides," J. CHEM. SOC. (1964) pp. 1467–1475 (Timms et al.); C. S. G. Phillips and P. L. Timms, "Some Applications of Gas Chromatography in Inorganic Chemistry", J. ANAL. CHEM. (April 1963) Vol. 35, No. 4 pp. 505–510. Other methods for preparing these materials include: pyrolysis of a germane with a silane; and the reaction of hydrofluoric acid on a mixed SiO-GeO preparation. See Timms et al.

A problem with these processes, however, is that they are not selective. That is, a number of different hydrides containing Group 4A atoms are formed. Thus, extensive purification is required to make a particular hydride by these processes. A more selective method for preparing these hydrides is therefore desirable.

One possible more selective route for preparing silicon and germanium hydrides containing two different Group 4A atoms that has been tried is the reaction of potassium silyl ($KSiH_3$) with a halide such as $CH_2Cl_2$, $CHCl_3$, or $CH_2Br_2$. J. A. Morrison and J. M. Bellama, "Synthesis and Characterization of the (Halosilyl) Methyl Silanes," JOURNAL OF ORGANOMETALLIC CHEMISTRY (1975) Vol. 92, pp. 167, report that this process route was found suitable for small-scale preparations of $(SiH_3)_2CH_2$. However, attempts to prepare this hydride on a larger scale at room temperature without solvent usually resulted in detonation.

Another problem with this process route is the difficulty and length of time it takes to prepare the starting material, potassium silyl ($KSiH_3$). M. A. Ring and D. M. Ritter "Preparation and Reactions of Potassium Silyl," J. AM. CHEM. SOC., (1960) Vol. 83, pp. 802 report that their preparations of potassium silyl ($KSiH_3$) using potassium metal and monosilane ($SiH_4$) took 60, 70, 74, and 76 days respectively. Ring and Ritter also report therein the preparation of sodium-potassium silyl from an alloy of sodium and potassium and monosilane ($SiH_4$) in 14 days. Starting with disilane ($Si_2H_6$), R. Varma and A. P. Cox, "A New Synthesis of Germylsilane," ANGEW. CHEM. Internat. Edit. (1964) Vol. 3, No. 8, p. 586, report the preparation of potassium silyl ($KSiH_3$) over a 24 hour period.

SUMMARY OF THE INVENTION

It is, therefore, an important object of the present invention to provide a process for preparing silicon and germanium hydrides containing two different Group 4A atoms which overcomes the above-mentioned drawbacks and problems.

It is a more specific object of the present invention to provide a process for preparing silicon and germanium hydrides containing two different Group 4A atoms which is more selective, less explosive and/or faster than previously known methods for preparing such materials.

A further object of the present invention is to provide deposition feedstock materials for use in the formation of hydrogenated amorphous silicon alloys in the fabrication of photovoltaic devices or other semiconductor devices.

Another object of the present invention is to provide novel coordinated salts of silicon and germanium hydride for use in preparing silicon and germanium hydrides containing two different Group 4A atoms.

Additional objects and advantages of the present invention will be set forth in part in the description which follows, and in part will be obvious from the description, or may be learned by practice of the invention. The objects and advantages of the invention may be realized and attained by means of instrumentalities and combinations particularly pointed out in the appended claims.

To achieve the objects, and in accordance with the purpose of the invention, as embodied and broadly described herein, the invention comprises a method for preparing a hydride containing at least two different Group 4A atoms wherein at least one of the Group 4A atoms is silicon or germanium, comprising the steps of: (a) reacting an alkali metal and a macrocyclic compound with a silicon or germanium hydride to form a salt; and (b) reacting the salt formed in step (a) with a halide containing a different Group 4A atom.

To further achieve the objects, and in accordance with the purpose of the invention, as embodied and broadly described herein, the invention also comprises a method for preparing a silicon germanium hydride comprising the steps of (a) reacting an alkali metal and a macrocyclic compound with a silicon or germanium hydride to form a salt; and (b) reacting the salt formed in step (a) with a silicon or germanium halide selected so that one of the hydride or halide contains silicon and the other contains germanium.

To further achieve the objects, and in accordance with the purpose of the invention, as embodied and broadly described herein, the invention additionally comprises a method for preparing a silicon carbon hydride comprising the steps of (a) reacting an alkali metal and a macrocyclic compound with a silicon hydride to form a salt; and (b) reacting the salt formed in step (a) with an organic halide.

To further achieve the objects, and in accordance with the purpose of the invention, as embodied and broadly described herein, the invention additionally comprises a coordinated salt of a Group 4A hydride comprising a cation and an anion wherein the cation is coordinated to a macrocyclic compound and the anion is a silicon hydride or a germanium hydride.

The foregoing and other objects, features, and advantages of the present invention will be made more apparent from the following description of the preferred embodiments.

BRIEF DESCRIPTION OF THE DRAWINGS

FIG. 1 is an illustration of a photovoltaic device (not to scale) which can be fabricated using the silicon or germanium hydrides made in accordance with the process of the present invention.

DESCRIPTION OF THE PREFERRED EMBODIMENTS

Reference will now be made in detail to the present preferred embodiments of the invention.

A method for preparing a hydride containing at least two different Group 4A atoms wherein at least one of the Group 4A atoms is silicon or germanium in accordance with the present invention comprises the steps of (a) reacting an alkali metal and a macrocyclic compound with a silicon or germanium hydride to form a salt; and (b) reacting the salt formed in step (a) with a halide containing a different Group 4A atom.

In accordance with the present invention, the salt formed in step (a) is a coordinated salt of a Group 4A hydride comprising a cation and an anion wherein the cation is coordinated to the macrocyclic compound and the anion is a silicon or germanium hydride.

The term Group 4A atom refers to atoms of the elements in Group 4A of the Periodic Table, i.e., carbon (C), silicon (Si), germanium (Ge), tin (Sn) and lead (Pb).

The term alkali metal refers to the metals in Group 1A of the Periodic Table, i.e., lithium (Li), sodium (Na), potassium (K), rubidium (Rb), cesium (Cs) and francium (Fr). The preferred alkali metals used in accordance with the present invention are lithium (Li), potassium (K) and sodium (Na).

As embodied herein, the term "macrocyclic compound" refers to a compound having 10 or more atoms in a ring. The term macrocyclic compound is intended to include both monocyclic and polycyclic macrocyclic compounds.

Macrocyclic compounds useful in the present invention include crown ethers, substituted crown ethers, cryptates and substituted cryptates. These materials are normally complex and have no encompassing general formulas. A representative but non-exhaustive list of examples of crown ethers useful in the practice of the present invention includes: 12-crown-4, 15-crown-5, and 18-crown-6. A representative but non-exhaustive list of examples of substituted crown ethers useful in the practice of the present invention includes: dibenzo-18-crown-6 ether, dibenzo-24-crown-8-ether, dicyclohexyl-18-crown-6-ether and dibenzo-15-crown-5-ether. A representative but non-exhausive list of examples of cryptates useful in the practice of the present invention includes: 2,2,2-cryptate, 2,2,1-cryptate and 2,1,1-cryptate. A representative but non-exhaustive list of examples of substituted cryptates useful in the practice of the present invention includes: alkyl-2,2,2-cryptate ether, benzo-2,2,2-cryptate.

In addition, analogs of crown ethers containing silicon, nitrogen or sulfur and analogs of cryptates containing nitrogen or sulfur are also useful in the practice of the present invention as they also form macrocyclic strucutres with large interior holes similar to the holes formed in the center of the crown ethers, substituted crown ethers, cryptates and substituted cryptates. Representative examples of structures of such analogs are:

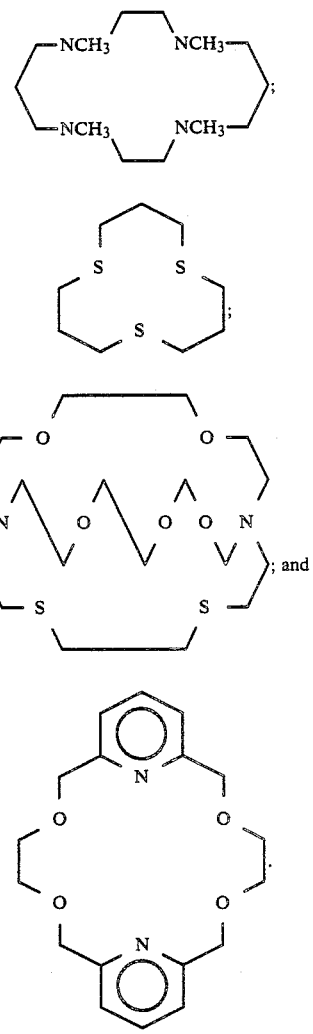

For purposes of the present invention, the macrocyclic compound used should be selected to complement the alkali metal which is being used. That is, the shape of the hole in the center of the macrocyclic compound should complement the size of the alkali metal. For example, with respect to crown ethers, 12-crown-4 is the preferred crown ether to use with lithium (Li) as the alkali metal. When sodium (Na) is used as the alkali metal, the preferred crown ether is 15-crown-5. 18-crown-6 is the preferred crown ether to use with the alkali metal potassium (K). Good results have been obtained using potassium as the alkali metal and 18-crown-6 as the macrocyclic compound to which it is coordinated.

For purposes of the present invention the hydride used in step (a) is either a silicon hydride or a germanium hydride. Selection of one or the other will depend on the final product desired.

The term silicon hydride refers to compounds of the formula:

$$Si_A M_B H_{(2(A+B)+2)}$$

wherein M is one or more Group 4A atoms. Preferably, for practicing the present invention the sum of A and B is an integer between 1 and 5, inclusive. A representative but not exhaustive list of examples of silicon hydrides useful in the practice of the present invention includes: $SiH_4$, $SiCH_6$, $SiGeH_6$, $Si_2CH_8$, $Si_2GeH_8$, $Si_3GeH_{10}$ and $Si_3CH_{10}$. The preferred silicon hydride to use in practicing the present invention is silane ($SiH_4$).

The term germanium hydride refers to compounds of the formula:

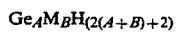

$$Ge_AM_BH_{2(A+B)+2}$$

wherein M is one or more Group 4A atoms. Preferably, for practicing the present invention the sum of A and B is an integer between 1 and 5 inclusive. A representative but not exhaustive list of preferred examples of germanium hydrides useful in the practice of the present invention includes: $GeH_4$, $GeCH_6$, $GeSiH_6$, $Ge_2CH_8$, $Ge_2SiH_8$, $Ge_3SiH_{10}$, and $Ge_3SiH_{10}$. The preferred germanium hydride to use in practicing the present invention is germane ($GeH_4$).

The halide containing a different Group 4A atom used in step (b) of the process of the present invention should also be selected on the basis of the desired end product. For example, if the end product desired is a silicon germanium hydride, then at least one of the halide and hydride should contain a silicon atom and at least one of the halide and hydride should contain a germanium atom. Alternatively, if the desired end product is a silicon carbon hydride, then a silicon hydride should be used with an organic halide. Similarly, if a germanium carbon hydride is desired, then a germanium hydride should be used with an organic halide.

A wide variety of halides containing a different Group 4A atom can be used in practicing step (b) of the present invention. Good results have been obtained using $CH_3I$, $CH_2Cl_2$, or $SiH_3Cl$ as the halide containing a different Group 4A atom.

As embodied herein, step (a), i.e., the salt formation step occurs at room temperature i.e, 20°-25° C. The pressure is preferably atmospheric pressure or above. Preferably an ether containing solvent is used. Preferred ether containing solvents include monoglyme ($CH_3OCH_2CH_2OCH_3$) and diglyme ($CH_3OCH_2CH_2OCH_2CH_2OCH_3$). Reaction time will vary depending on the hydride used. Agitation of the reaction mixture is preferred. Typical reaction times range from 30 minutes to 24 hours with suitable agitation.

As embodied herein step (b), i.e., the reaction with a halide step is exothermic. Consequently, it is preferable to cool the reactants and then let the reaction mixture warm to room temperature. Preferably, the reactants are cooled to a temperature of between $-100°$ C. and 0° C. The best temperature within this range will vary depending on the particular solvents and reactants used. The reaction is largely independent of pressure and thus any suitable pressure can be used. Atmospheric pressure or below is preferred since too high a pressure may slow down the voltization of the product. Reaction time is dependent on how fast the reaction mixture is warmed to room temperature. Preferably, this is done in less than 30 minutes.

The above reactions need to be performed in the absence of water and oxygen to avoid undesirable side reactions with the cation or the hydride. The resulting products can be analyzed and identified with standard instrumentation such as gas chromatograph (GC)/mass spectrometer (mass spec). Typically, by-products include the starting hydride and halide as well as reduced forms of the halide. These by-products and any excess solvent can be removed relatively easily by standard methods of distillation.

In order to illustrate the merits of the present invention and the significant advantages of the present invention over prior art processes for making silicon and germanium hydrides containing two different Group 4A atoms, reference is made to the following examples.

EXAMPLE 1

Preparation of $SiH_3Cl$ As a Starting Material for the Preparation of $SiH_3GeH_3$ A 500 ml gas bulb was evacuated and filled with nitrogen. 3 ml of tin tetrachloride ($SnCl_4$) (Alfa Products ®) and 0.56 gms of silane ($SiH_4$) (Airco ®) were added to the bulb. The bulb was sealed off and allowed to sit overnight (15–19 hours) at room temperature. The product was distilled and silylchloride ($SiH_3Cl$) was collected.

EXAMPLE 2

Preparation of $SiH_3GeH_3$

A 250 cc flask was degassed 0.195 gm of potassium (K) (Alfa Products ®) and 1.58 gm of 18-crown-6 (Aldrich ®) were added to the flask while flushing the flask with nitrogen. Four ml of distilled monoglyme ($CH_3OCH_2CH_2OCH_3$) (Aldrich ®) was added to the flask while continuing to flush with nitrogen. The flask was then sealed and frozen in liquid nitrogen. Nitrogen was then evacuated from the flask and 0.38 gm of germane ($GeH_4$) (Matheson ®) was added to the flask. After sealing, the flask was warmed to room temperature while stirring the reaction mixture for 30 minutes to obtain [K 18-crown-6]$^+$GeH$_3^-$.

Solvent was drawn from the flask with a vacuum pump and the flask was then frozen in liquid nitrogen. 0.30 gm of $SiH_3Cl$ prepared in Example 1 was added to the flask, and the flask was sealed. Over 15 minutes the flask was allowed to warm to room temperature. The reaction product was then collected in a liquid nitrogen trap. The sample was analyzed by GC/mass spec and a yield of 5% $SiH_3GeH_3$ was obtained. Other by-products also present in the reaction product were silane and germane.

EXAMPLE 3

Preparation of $SiH_3CH_3$

A 250 cc flask was degassed. 0.225 gm of potassium (K) (Alfa Products ®) and 1.94 gm of 18-crown-6 (Aldrich ®) were added to the flask while flushing the flask with nitrogen. Six ml of distilled monoglyme (Aldrich ®) was added to the flask while continuing to flush with nitrogen. The flask was sealed and frozen in liquid nitrogen. The nitrogen was evacuated from the flask and 0.16 gm of silane ($SiH_4$) (Airco ®) was added to the flask. After sealing with a stopcock, the flask was warmed to room temperature while stirring the reaction mixture for 3 hours to obtain [K 18-crown-6]$^+$SiH$_3^-$.

Solvent was drawn from the flask with a vacuum pump and the flask was then frozen in liquid nitrogen. 1 gm of methyl iodide ($CH_3I$) (Aldrich ®) was added and the flask was sealed. The reaction was allowed to proceed for 2 hours at $-38°$ C. Product was then collected in a liquid nitrogen trap. The sample was analyzed by GC/mass spec and a yield of 90% $SiH_3CH_3$ was obtained. Other by-products also present in the reaction product were methane, silane and ethane.

EXAMPLE 4

Preparation of $SiH_3CH_2SiH_3$

A 250 cc flask was degassed. 0.235 gm of potassium (K) (Alfa Products ®) and 2.0 gm of 18-crown-6 (Aldrich ®) were added to the flask while flushing the flask with nitrogen. Eight ml of distilled monoglyme (Aldrich ®) was added to the flask while continuing to flush with nitrogen. The flask was sealed and then frozen in liquid nitrogen. The nitrogen was evacuated from the flask and then 0.25 gm of $SiH_4$ (Airco ®) was added to the flask. After sealing, the flask was warmed to room temperature while stirring the reaction mixture overnight (approximately 15-18 hours) to obtain [K 18-crown-6]$^+SiH_3^-$.

Solvent was drawn from the flask with a vacuum pump and the flask was frozen in liquid nitrogen. 0.2 gm of methylene chloride ($CH_2Cl_2$) (Aldrich) was added to the flask and the flask was sealed. Over 15 minutes the flask was allowed to warm to room temperature. Product was collected in a liquid nitrogen trap. The sample was analyzed by GC/mass spec and a yield of 19% $SiH_3CH_2SiH_3$ was obtained. Other by-products also present in the reaction product were silane, methylsilane and chloromethylsilane.

EXAMPLE 5

Repeat Preparation of $SiH_3CH_2SiH_3$

A 250cc flask was degassed. 0.235 gm of potassium (K) (Alfa Products ®) and 2.0 gm of 18-crown-6 (Aldrich ®) were added to the flask while flushing the flask with nitrogen. 100 ml of distilled monoglyme (Aldrich ®) was added to the flask while continuing to flush with nitrogen. The flask was sealed and frozen in liquid nitrogen. The nitrogen was evacuated from the flask and 0.25 gm of $SiH_4$ was added to the flask. After sealing, the flask was warmed to room temperature while stirring the reaction mixture overnight (15-18 hours) to obtain [K 18-crown-6]$^+SiH_3^-$.

Solvent was drawn from the flask with a vacuum pump and the flask was frozen in liquid nitrogen. 0.2 gm of $CH_2Cl_2$ (Aldrich ®) was added to the flask and the flask was sealed. Over 15 minutes the flask was allowed to warm to room temperature. Poduct was collected in a liquid nitrogen trap. The sample was analyzed by GC/mass spec and a yield of 36% $SiH_3CH_2SiH_3$ was obtained. Other by-products present in the reaction product were silane, methylsilane, disilane, and chloromethylsilane.

The Group 4A hydrides made in accordance with the process of the present invention are useful as deposition feedstock materials in the formation of hydrogenated amorphous silicon alloys used in the fabrication of photovoltaic devices. This is discussed in greater detail in copending U.S. patent application Ser. No. 06/830,073 of Charles Robert Dickson, entitled "Deposition Feedstock Materials Useful in the Fabrication of Amorphous Silicon Alloys for Photovoltaic Devices," filed concurrently herewith, the disclosure of which is incorporated herein by reference.

As is explained therein, it is preferable to include different atoms from Group 4A of the Periodic Table, such as carbon and germanium, in hydrogenated amorphous silicon alloys in order to adjust their optical bandgap. For example, carbon has a larger bandgap than silicon and thus inclusion of carbon in a hydrogenated amorphous silicon alloy increases the alloy's bandgap. Conversely, germanium has a smaller bandgap than silicon and thus inclusion of germanium in such an alloy decreases the alloy's bandgap.

Hydrogenated amorphous silicon alloy films are conventionally prepared by glow discharge deposition in a deposition chamber. By including a silicon or germanium hydride made in accordance with the present invention as a deposition feedstock material included in the deposition gas mixture introduced into the deposition chamber, the incorporation of desired Group 4A atoms into the hydrogenated amorphous silicon alloy can be better controlled and undesirable dangling electron bonds can be reduced or eliminated.

FIG. 1 is an illustration of a photovoltaic device which can be fabricated using the silicon or germanium hydrides made in accordance with the process of the present invention. As shown in FIG. 1, light (1) enters the light incident side of the photovoltaic cell. The light passes first through a glass layer (2), then through a transparent conductive layer (3) and then into a multilayered hydrogenated amorphous silicon region (4). Lastly, on the side opposite the light incident side of the photovoltaic device is a metal back contact (5).

In FIG. 1, the multilayered amorphous silicon region (4) is a p-i-n junction. That is, the multilayered amorphous silicon region includes a positively doped layer (p-layer) (6), an intrinsic layer i-layer) (7) and a negatively doped layer (n-layer) (8). A conventional hydrogenated amorphous silicon photovoltaic cell having a p-i-n junction of this same general form is shown, for example, in U.S. Pat. No. 4,217,148, the disclosure of which is incorporated by reference herein.

In accordance with a preferred embodiment of the present invention, a silicon germanium hydride is prepared by the steps of (a) reacting an alkali metal and a macrocyclic compound with a silicon or germanium hydride to form a salt; and (b) reacting the salt formed in step (a) with a silicon or germanium halide selected so that one of the hydride or halide contains silicon and the other contains germanium. Silicon germanium hydrides prepared by this method are particularly suitable as deposition feedstock materials for forming i-layers or n-layers in p-i-n type photovoltaic devices such as is illustrated in FIG. 1.

In accordance with another preferred embodiment of the present invention, a silicon carbon hydride is prepared by the steps of (a) reacting an alkali metal and a macrocyclic compound with a silicon hydride to form a salt and (b) reacting the salt formed in step (a) with an organic halide. Silicon carbon hydrides prepared by this method are particularly suitable as deposition feedstock material for forming p-layers in p-i-n type photovoltaic devices such as illustrated in FIG. 1.

Examples 6 and 7 illustrate uses of the silicon and germanium hydrides made by the process of the present invention in the formation of hydrogenated amorphous silicon alloy layers in the fabrication of p-i-n junctions such as is illustrated in FIG. 1.

EXAMPLE 6 (proposed)

A 100 Å thick amorphous silicon carbon p-layer is formed using a deposition gas mixture containing 15 SCCM of disilylmethane, $(SiH_3)_2CH_2$, prepared by the method described in example 5, 12 SCCM of 1½% diborane, $B_2H_6$, in silane, $SiH_4$, and 73 SCCM of silane. The p-layer is deposited in a D.C. glow discharge using a cathode current density of 0.14 ma/cm$^2$, a substrate temperature of 220° C. and a total gas pressure of 0.5 torr.

EXAMPLE 7 (proposed)

A 2500 Å thick amorphous silicon germanium i-layer is formed using a deposition gas mixture containing 5 SCCM of monosilylgermane, $SiH_3GeH_3$, prepared by the method described in example 2, and 95 SCCM of silane, $SiH_4$. The i-layer is deposited in a D.C. glow discharge using a cathode current density of 0.09 ma/cm$^2$, a substrate temperature of 220° C. and a total gas pressure of 0.5 torr.

It will be apparent to those skilled in the art that various modifications and variations can be made in the present invention without departing from the scope or spirit of the invention. Thus, it is intended that the present invention cover the modifications and variations of this invention provided that they come within the scope of the appended claims or their equivalents.

What is claimed is:

1. A method for preparing a hydride containing at least two different Group 4A atoms, wherein at least one of said Group 4A atoms is silicon or germanium, said method comprising the steps of:
   (a) reacting an alkali metal and a macrocyclic compound selected to be able to hold said alkali metal to form a reaction product and then reacting said reaction product with a silicon hydride or a germanium hydride to form a salt; and
   (b) reacting said salt formed in step (a) with a Group 4A halide containing a different Group 4A atom.

2. The method of claim 1 wherein said hydride is silane or germane.

3. The method of claim 1 wherein said macrocyclic compound is a crown ether, a substituted crown ether, a cryptate or a substituted cryptate.

4. The method of claim 1 wherein said alkali metal is potassium and said macrocyclic compound is the crown ether, 18-crown-6.

5. A method for preparing a silicon germanium hydride, comprising the steps of: (a) reacting an alkali metal and a macrocyclic compound selected to be able to hold said alkali metal to form a reaction product and then reacting said reaction product with a silicon hydride or a germanium hydride to form a salt; and (b) reacting said salt formed in step (a) with a silicon halide or a germanium halide selected so that one of the hydride or halide contains silicon and the other contains germanium.

6. The method of claim 5 wherein said hydride is silane or germane.

7. The method of claim 5 wherein said macrocyclic compound is a crown ether, a substituted crown ether, a cryptate or a substituted cryptate.

8. The method of claim 5 wherein said alkali metal is potassium and said macrocyclic compound is the crown ether, 18-crown-6.

9. The method of claim 5 wherein said hydride is germane and said halide is chlorosilane.

10. A method for preparing a silicon carbon hydride comprising the steps of: (a) reacting an alkali metal and a macrocyclic compound selected to be able to hold said alkali metal to form a reaction product and then reacting said reaction product with a silicon hydride to form a salt; and (b) reacting said salt formed in step (a) with an organic halide.

11. The method of claim 10 wherein said hydride is silane.

12. The method of claim 10 wherein said macrocyclic compound is a crown ether, a substituted crown ether, a cryptate or a substituted cryptate.

13. The method of claim 10 wherein said alkali metal is potassium and said macrocyclic compound is the crown ether, 18-crown-6.

14. The method of claim 11 wherein said halide is $CH_3I$.

15. The method of claim 11 wherein said halide is $CH_2Cl_2$.

* * * * *